US00PP26915P3

(12) United States Plant Patent
MacIlvaine et al.

(10) Patent No.: US PP26,915 P3
(45) Date of Patent: Jul. 12, 2016

(54) PISTACHIO ROOTSTOCK TREE NAMED 'WONDERFUL PISTACHIO ROOTSTOCK #2'

(50) Latin Name: *Pistacia atlantica×P. integerrima*
Varietal Denomination: Wonderful Pistachio Rootstock #2

(71) Applicant: Wonderful Orchards LLC, Shafter, CA (US)

(72) Inventors: Joseph MacIlvaine, Bakersfield, CA (US); Eric Mercure, Bakersfield, CA (US); John Etchamendy, Wasco, CA (US)

(73) Assignee: Wonderful Orchards LLC, Shafter, CA (US)

( * ) Notice: Subject to any disclaimer, the term of this patent is extended or adjusted under 35 U.S.C. 154(b) by 0 days.

(21) Appl. No.: 13/998,774

(22) Filed: Dec. 4, 2013

(65) Prior Publication Data

US 2015/0156936 P1 Jun. 4, 2015

(51) Int. Cl.
*A01H 5/00* (2006.01)

(52) U.S. Cl.
USPC ..... Plt./152

(58) Field of Classification Search
USPC ..... Plt./152
See application file for complete search history.

*Primary Examiner* — June Hwu

(74) *Attorney, Agent, or Firm* — Knobbe, Martens, Olson & Bear, LLP

(57) ABSTRACT

A new and distinct variety of pistachio tree characterized by producing large leaves, reddish-green new foliage, and dark green mature foliage. The new variety is useful as a rootstock for commercial nut bearing pistachio varieties.

3 Drawing Sheets

Latin name of the genus and species claimed: '*Pistacia atlantica*'×'*P. integerrima*'.

Variety denomination: 'WONDERFUL PISTACHIO ROOTSTOCK #2'.

BACKGROUND AND SUMMARY OF THE INVENTION

This invention relates to the discovery and asexual propagation of a new and distinct variety of Pistachio tree, '*Pistachia atlantica×P. integerrima*, cv. 'Wonderful Pistachio Rootstock #2' as herein described and illustrated. The new variety is a hybrid of *P. atlantica* and *P. integerrima* which was first discovered on cultivated land from trees grown from seed produced by a cross of the two parent species. The new variety was discovered and further characterized, and propagated by Joseph MacIlvaine, Eric Mercure and John Etchamendy in the San Joaquin Valley, Kern County, Calif. The initial discovery, characterization and propagation of the new variety took place from 2006 to 2010.

The new variety 'Wonderful Pistachio Rootstock #2' is characterized by producing large leaves, reddish-green new foliage, dark green mature foliage and upright habits with rounded crown. The new variety is useful as a rootstock to nut bearing pistachio.

The new variety Paramount 'Wonderful Pistachio Rootstock #2' was first asexually propagated in 2009 by Eric Mercure by meristem or shoot tip tissue culture at Southern San Joaquin Valley in Kern County, Calif. and established and transmitted through succeeding propagation by air-layering.

The male parent is '*P. integerrima*' and the female parent is '*P. atlantica*'. The date of first sowing was 1990, and the date of first flowering was 1996.

The new variety 'Wonderful Pistachio Rootstock #2' differs from its male parent *P. integerrima* in that the leaves and leaflets are shorter. Also, the leaflet base is more rounded in the new variety. In addition, the leaves are less red when emerging and fall off sooner.

The new variety 'Wonderful Pistachio Rootstock #2' differs from its female parent '*P. atlantica*' in that new variety is more vigorous and is believed to be more resistant to verticillium disease. The leaflets of the new variety are larger and less rounded with a faster growth rate. The new variety has an overall larger size canopy.

The new variety can be distinguished from other available varieties by its yield characteristics. The closest available varieties are 'Pioneer Gold' and 'UCB1', an *P. atlantica×P. integerrima* hybrid. Yields on *P. vera* have been observed to be consistently higher on mature trees on the new rootstock variety when compare to 'Pioneer Gold' and 'UCB1'. The new variety 'Wonderful Pistachio Rootstock #2' can also be distinguished from 'Pioneer Gold' by the leaf shape.

The new 'Wonderful Pistachio Rootstock #2' variety has been shown to maintain its distinguishing characteristics through successive asexual propagations by, for example, meristem or shoot tip tissue culture and air layering.

Variations of the usual magnitude from the characteristics described herein may occur with changes in growing conditions, irrigation, fertilization, pruning, management and with climatic variation.

The new variety 'Wonderful Pistachio Rootstock #2' was analyzed to identify unique molecular markers. In one set of experiments, primers were used to amplify a variety of simple sequence repeats (SSRs), essentially as described in Vendramin et al. Mol. Ecology Res. (2010) 10(3):576-579. SSRs were identified from a GT-enriched library prepared from *P. atlantica* and *P. intergerrima* DNA and from the literature (Vendramin et al., Ahmad et al. J. Amer. Soc. Hort. Sci. (2003) 128(6):898-903 and Albaladejo et al. Mol. Ecology Res. (2008) 8:904-906). Primers were prepared and used to amplify relevant loci. 'Wonderful Pistachio Rootstock #2' was compared to its parents *P. atlantica* and *P. integerrima*, as well as 'UCB1' and two unpatented varieties. 'Wonderful Pistachio Rootstock #2' was uniquely identified in this group by the presence of products at about 244:252 bp generated using a primer set corresponding to EPV F034 from Vendramin et al. combined with the lack of products produced from primer set EPV F013 from Vendramin et al.

DNA amplification fingerprinting (DAF) was also used to analyze 'Wonderful Pistachio Rootstock #2', essentially as described in Caetano-Anolles BioTechniques (1998) 25:472-480 and Trigiano, R. N. and G. Caetano-Anolles. HortTechnology (1998) 8(3):413-423. Two DAF primers, 8.6D and 8.6J (Trigiano, R. N. et al. HortTechnology (2004) 39(3):489-492) were able to distinguish 'Wonderful Pistachio Rootstock #2' from 'UCB1' and two unpatented varieties. Primer 8.6D produced a singlet at about 450 bp in 'Wonderful Pistachio Rootstock #2'. The singlet was not present in 'UCB1', 'Wonderful Pistachio Rootstock #1' (U.S. Plant patent application Ser. No. 13/998,771) or in the two unpatented varieties. Primer 8.6J was also able to distinguish 'Wonderful Pistachio Rootstock #2' from 'UCB1', as it produced a single band at about 425 bp in 'Wonderful Pistachio Rootstock #2' but not in 'UCB1'. In Wonderful Pistachio Rootstock #1 Primer 8.6J produced heavy bands at 150-200 bp.

BRIEF DESCRIPTION OF THE DRAWINGS

The accompanying color photographic illustrations

Figure 1:
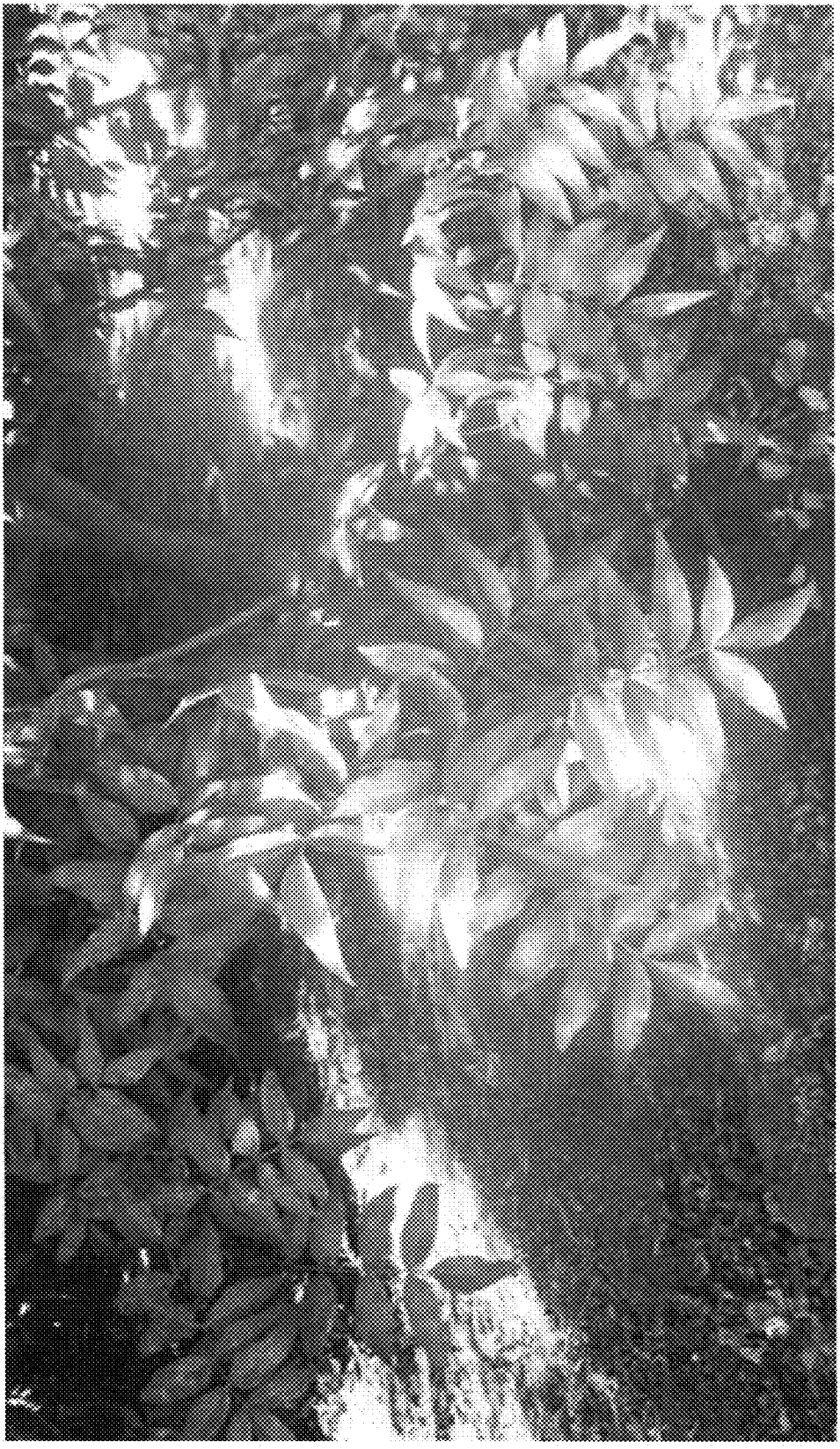
FIGS. 1 and 2 show a close up of the foliage of the new variety 'Wonderful Pistachio Rootstock #2'.
Figure 2:
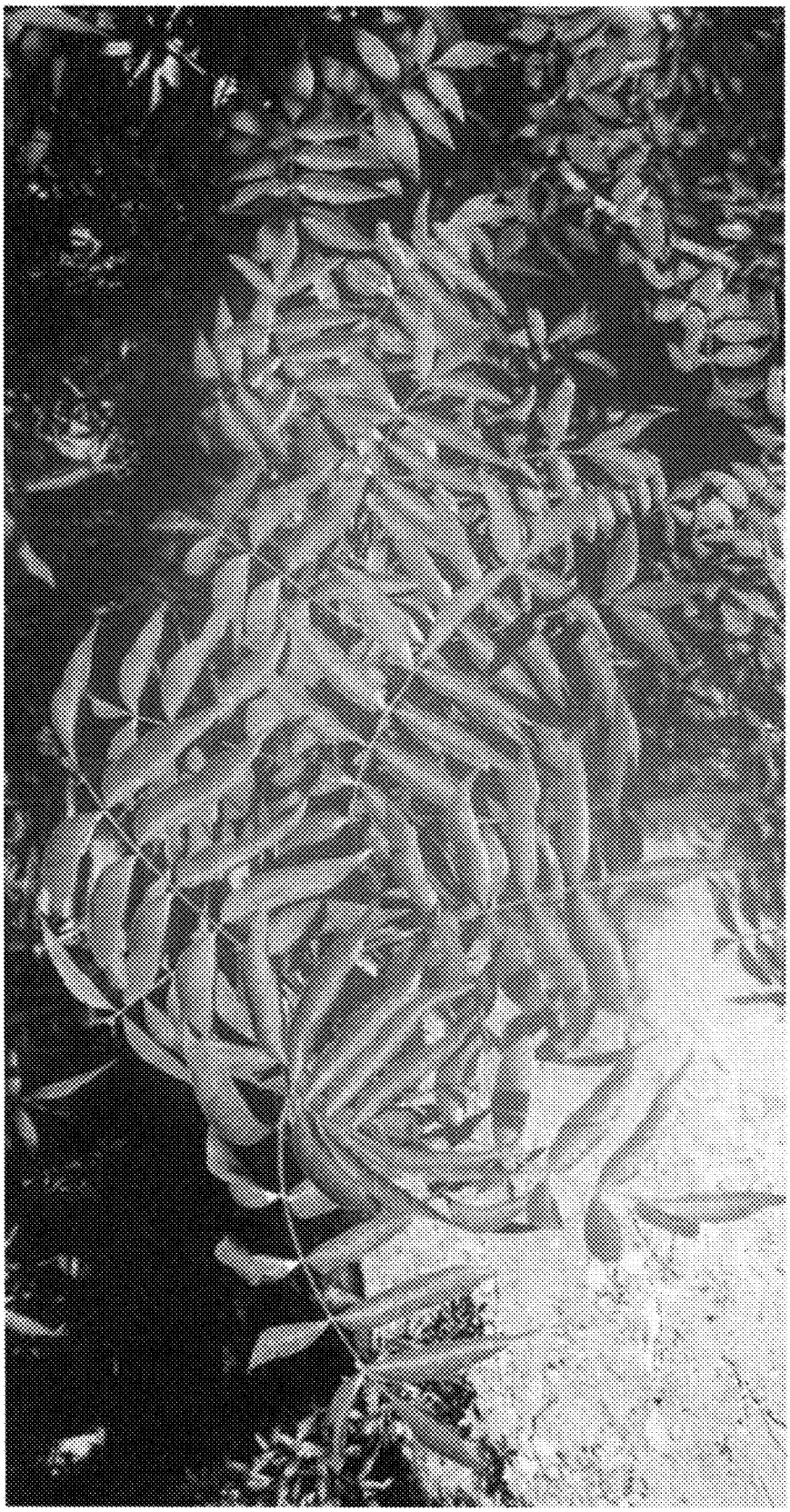
Figure 3:
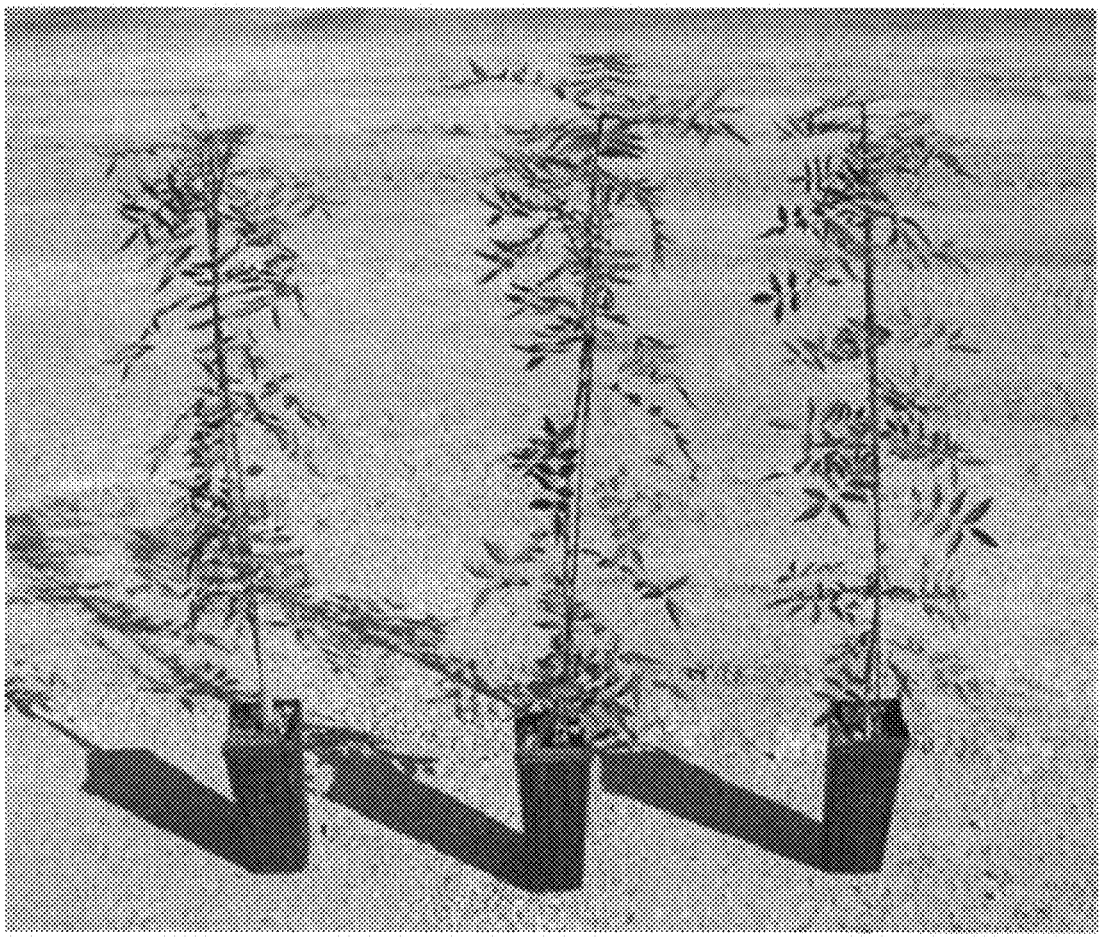
FIG. 3 show potted nursery trees that are ready to be budded. Wonderful Pistachio Rootstock #2 is the tree in the middle in FIG. 3.

The colors of photographic illustration are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 5$^{th}$ edition, 2007.

The descriptive matter which follows pertains to 'Wonderful Pistachio Rootstock #2' grown in the vicinity of the Southern San Joaquin Valley in Kern County, Calif. during 2002 to present, and is believed to apply to plants of the variety grown under similar conditions of soil and climate elsewhere.

PLANT

General:

*Growth*.—Upright tree with a rounded crown reaching 70-100 feet in height.

Leaf rachis:

*Color*.—About Medium Green 139C on the upper side with some Medium Red-Purple 64B on leaves closer to ground. About Light Green 141D on the lower side.

*Length*.—Approximately 5.25 in to 5.75 in.

The description below was taken from 9 to 18 month old nursery trees:

FOLIAGE

Leaves:

*Number of leaflets*.—9-11 sometimes 7.

*Average length*.—Approximately 6 to 7.5 inches.

*Average width*.—Approximately 2.75 to 3.5 inches.

Leaflets:

*Size*.—Medium, approximately 3 inches (1.25 to 2.25 inches in length, ⅜ to ⅝ inches in width).

*Shape*.—Lanceolate.

*Length*.—Medium, approximately 2.5-3 inches.

*Color of new leaflets*.—About Dark Greyed-purple 183B for both upper and lower leaf surface.

*Color of old leaflets*.—Upper surface is about Dark Green 137A, Dark Green 137B and Yellow-Green 147B. Lower surface is about Dark Green 137B.

*Edge*.—Entire.

*Petiole*.—Petiolated.

*Arrangement of petiolule*.—Pinnately compound.

*Arrangement of leaflets*.—Alternate.

*Shape of leaf at apex*.—Acuminate.

*Shape of leaf at base*.—Acute.

*Margin*.—Entire.

*Venation*.—Pinnate.

*Vein color*.—About Dark Green 137A, Dark Green 137B and Yellow-Green 147B.

*Texture of top surface*.—Glabrous.

*Texture of bottom of surface*.—Glabrous.

Ribs:

*Length*.—Approximately 5.25 to 5.75 inches.

*Color*.—About Dark Greyed-Purple 183A-B on both sides of new leaflets. Medium Yellow-Green 139C to 144A-B on the top surface and underside color about Light Green 141D to about medium Yellow-Green 144B in older leaflets.

Petiole:

*Length*.—Approximately 1.25 to 2.5 inches.

*Color*.—Same color as the ribs.

*Diameter*.—Less than ⅛ inch.

Veins, ribs, and petiole have some about medium red-purple 64B coloring on leaves growing closer to the ground.

Growth:

*Trunk shape*.—Upright.

*Height*.—Trees are grown 2 to 3 ft in height before they are grafted with *P. vera* 'Kerman or *P. vera* 'Peters' bud. Trees are not allowed to grow to maturity. Stem color: About Medium Grey-Brown 199D with lenticels Medium Greyed-Orange 177D. Fissures are Dark Brown about 200B. Stem diameter: Large, approximately 0.033 to 0.05 inches for trees at 2 to 3 ft. in height.

*Bark texture*.—Smooth, slightly striated when young.

*Vegetative bud size*.—Approximately ⅛"-¼".

*Vegetative bud color*.—Reddish-gray, mostly About Dark Greyed-Orange 179A with some About Medium Brown 200D.

The description below was taken from 7 TO 9 year old trees:

FOLIAGE

Leaves:

*Number of leaflets*.—9-11 sometimes 7.

*Average length*.—Long, approximately 7.5 to 9 inches.

*Average width*.—Medium, approximately 4.25 to 3.5 inches.

Leaflets:

*Size*.—Medium, approximately 3 inches (3 to 3.825 inches in length, 0.75 to 1.125 inches in width).

*Shape*.—Lanceolate.

*Color of new leaflets*.—About Dark Greyed-purple 183B for both upper and lower leaf surface.

*Color of old leaflets*.—Upper surface is about Dark Green 136A, Dark Green 137B and Yellow-Green 147B. Lower surface is about Dark Green 137B.

*Edge*.—Entire.

*Petiole*.—Petiolated.

*Arrangement of petiolule*.—Pinnately compound.

*Arrangement of leaflets*.—Alternate.

*Shape of leaf at apex*.—Acuminate.

*Shape of leaf at base*.—Acute.

*Margin*.—Entire.

*Venation*.—Pinnate.

*Vein color*.—About Dark Green 137A, Dark Green 137B and Yellow-Green 147B.

*Texture of top surface*.—Glabrous.

*Texture of bottom of surface*.—Glabrous.

Ribs:

*Length*.—Approximately 5.25 to 5.75 inches.

*Color*.—About Dark Greyed-Purple 183A-B to 139C Medium Green to Medium Yellow-Green 144A-B on the upper surface, and underside color about Light Green 141D to about Medium Yellow-Green 144B.

Petiole:

*Length*.—Approximately 1.25 to 2.5 inches.

*Color*.—About Dark Greyed-Purple 183B to Medium Yellow-Green 144A-B.

*Diameter*.—Less than ⅛ inch.

Branch:

*Size*.—Approximately 2 ft to 4 ft in a single season.

*Surface texture*.—Smooth when young and slightly furrowed with ridges when older.

GROWTH

*Trunk shape*.—Upright.

*Stem color*.—About Medium Grey-Brown 199D with fissures About Dark Brown 200B. Color ranges from About Medium Grey-Brown 199D with Medium Greyed-Orange 177D lenticels.

*Trunk diameter*.—Large, approximately 0.033 to 0.05 inches.

*Bark texture*.—Striated when young and slightly furrowed with age.

*Vegetative bud size*.—Approximately 0.25 inches to 0.5 inches.

*Vegetative bud color*.—Reddish-gray, a mixture of About Light Green 143D and About Medium Greyed-Orange 179D.

What is claimed is:

1. A new and distinct variety of pistachio tree as herein illustrated and described.

* * * * *